United States Patent
Münter et al.

(10) Patent No.: US 6,197,780 B1
(45) Date of Patent: Mar. 6, 2001

(54) METHOD FOR COMBATING OBESITY

(75) Inventors: Klaus Münter; Michael Kirchengast, both of Mannheim (DE)

(73) Assignee: Knoll Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/530,131

(22) PCT Filed: Nov. 21, 1998

(86) PCT No.: PCT/EP98/07501

§ 371 Date: Apr. 27, 2000

§ 102(e) Date: Apr. 27, 2000

(87) PCT Pub. No.: WO99/29308

PCT Pub. Date: Jun. 17, 1999

(30) Foreign Application Priority Data

Dec. 5, 1997 (DE) ............................................. 197 54 082

(51) Int. Cl.[7] .................................................. A61K 31/505
(52) U.S. Cl. ............................................................ 514/274
(58) Field of Search ................................................ 514/274

(56) References Cited

FOREIGN PATENT DOCUMENTS 670 320    9/1995   (EP) .
97/08169   3/1997   (WO) .

OTHER PUBLICATIONS

Galluzzi et al. Hormone Research vol. 48, No. 2, Suppl. 2 pp. 183 (1997).
Hauner, Int. Journal of Obesity, vol. 18, Supp. 2, pp. 147 (1994).
British J.ofPhar (1995)116,2482–2486, Allcock et al.
Kaddoura et al.,Circulation, vol. 93, No. 11 pp. 2068–2079, (1996).
Eur.J.Phar.294(1995)183–189,Bird et al.
Derwent Abs. of JP 10 194 72 A (Tavrbe)(1998).
Parrinello et al. Am. J. Circulation, vol. 9, No. 12, Part 1. 1996;1186–1191.

*Primary Examiner*—Raymond Henley, III
(74) *Attorney, Agent, or Firm*—Keil & Weinkauf

(57) ABSTRACT

Diseases caused by obesity are treated with endothelin receptor antagonists. Diseases treated include those frequently associated with obesity such as hypertension, type 2 diabetes, hyperlipidemia, chronic kidney failure, arteriosclerosis and gout.

4 Claims, No Drawings

METHOD FOR COMBATING OBESITY

This is a 371 of PCT/EP98/07501 filed Nov. 21, 1998.

The present invention relates to a method for controlling obesity and diseases caused by obesity.

The peptide hormone endothelin is known for its strong vasoconstrictor properties. Endothelin receptor antagonists are therefore mainly being tested in cardiovascular pathologies.

The invention relates to the use of endothelin receptor antagonists for producing drugs for controlling obesity and diseases caused by obesity.

The endothelin receptor antagonists which can be used are both endothelinA and mixed endothelinA/B receptor antagonists.

Particularly suitable endothelin receptor antagonists are
1. TBC-11251 (J. Med. Chem., 40, No. 11, 1690–97, 1997),
2. BMS-193884 (EP 558.258)
3. BMS-207940 (Pharmaprojects (13.06.97)),
4. BQ-123 (Exp. Opin. Invest. Drugs, 1997, 6, No. 5, 475–487),
5. SB-209670 (Exp. Opin. Invest. Drugs, 1997, 6, No. 5, 475–487),
6. SB-217242 (Exp. Opin. Invest. Drugs, 1997, 6, No. 5, 475–487),
7. SB-209598 (Trends in Pharmacol. Sci., 17, 177–81, 1996),
8. TAK-044 (Exp. Opin. Invest. Drugs, 1997, 6, No. 5, 475–487),
9. Bosentan (Trends in Pharmacol. Sci., 18, 408–12, 1997),
10. PD-156707 (J. Med. Chem., 40, No. 7, 1063–74, 1997),
11. L-749329 (Bioorg. Med. Chem. Lett., 7, No. 3, 275–280, 1997),
12. L-754142 (Exp. Opin. Invest. Drugs, 1997, 6, No. 5, 475–487),
13. ABT-627 (J. Med. Chem., 40, No. 20, 3217–27, 1997),
14. A-127772 (J. Med. Chem., 39, No. 5, 1039–1048, 1996),
15. A-206377 (213th American Chemical Society National Meeting, San Francisco, Calif., USA, Apr. 13–17, 1997, Poster, MEDI 193),
16. A-182086 (J. Med. Chem., 40, No. 20, 3217–27, 1997),
17. EMD-93246 (211th American Chemical Society National Meeting, New Orleans, USA, 1996, Poster, MEDI 143),
18. EMD-122801 (Bioorg. Med. Chem. Lett., 8, No. 1, 17–22, 1998),
19. ZD-1611 (Trends in Pharmacol. Sci., 18, 408–12, 1997),
20. AC-610612 (R&D Focus Drug News (18.05.98)),
21. T-0201 (70th Annual Meeting of the Japanese Pharmacological Society, Chiba, Japan, Mar. 22–25 1997, Lecture, O-133),
22. J-104132 (R&D Focus Drug News (15.12.97)) and, in particular,

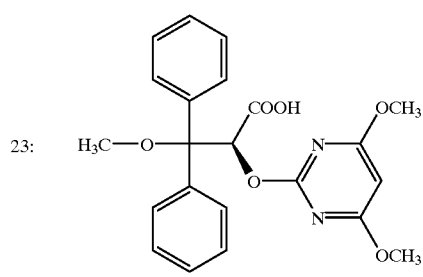

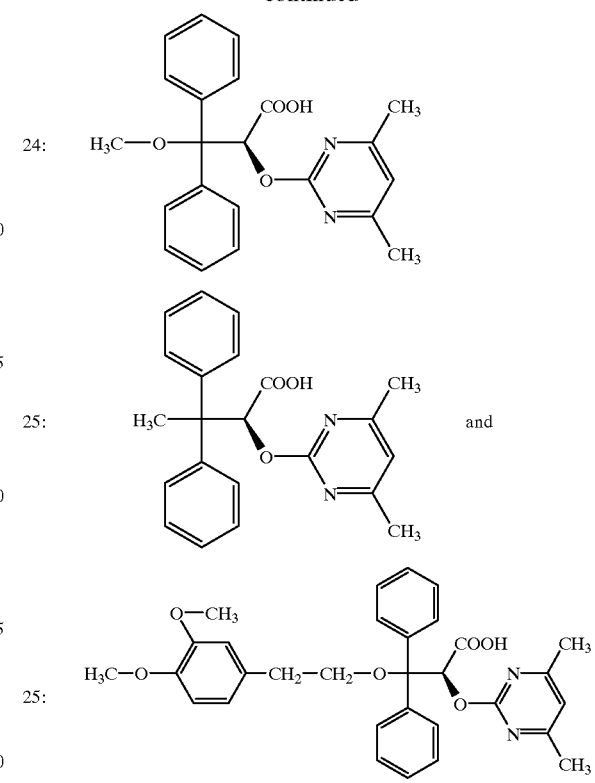

Obesity is the term used when the bodyweight is at least 20% over the normal weight. The causes of obesity are overeating or faulty utilization of food, for example familial hypercholesterolemia. Diseases caused by or frequently associated with obesity which should be specifically mentioned are hypertension, type 2 diabetes, hyperlipidemia, chronic kidney failure and arteriosclerosis and possibly also gout.

It has to date been possible only with great difficulty to simulate the pathological state of obesity in animal experiments (administration of extremely high cholesterol doses). However, recently, knockout mice lacking the gene for apolipoprotein E have been bred and can be employed for testing substances to counter obesity.

The effect of the endothelin receptor antagonist substance 23 was investigated in the animal model of the apoE knockout mouse. In control rats, as was to be expected, the bodyweight of the animals on a high-fat diet increased greatly. This was associated with an increase in the size of the liver with simultaneous fatty degeneration of the liver. In a parallel group, the animals were treated with substance 23 (50 mg/kg/d). In this group, the increase in body and liver weight was completely prevented. The liver was also histologically unremarkable.

The endothelin$_A$ and endothelin$_{A/B}$ receptor antagonists must be administered life-long. Their dosage is from 50 to 500 mg per patient and day.

Endothelin$_A$ and endothelin$_{A/B}$ receptor antagonists are generally administered orally, for example in the form of uncoated, lacquered and sugar-coated tablets, hard and soft gelatin capsules, solutions, emulsions or suspensions. However, administration may also take place rectally, for example in the form of suppositories, or parenterally, for example in the form of injection solutions.

To produce uncoated, lacquered and sugar-coated tablets and hard gelatin capsules, a combination according to the invention can be processed with pharmaceutically inert, inorganic or organic excipients. Excipients of these types which can be used for uncoated and sugar-coated tablets and hard gelatin capsules are lactose, corn starch or derivatives thereof, talc, stearic acid or its salts. Excipients suitable for soft gelatin capsules are vegetable oils, waxes, fats, semi-solid and liquid polyols.

Excipients suitable for producing solutions and syrups are, for example, water, polyols, sucrose, invert sugar, glucose and the like. Excipients suitable for injection solutions are water, alcohols, polyols, glycerol, vegetable oils. Excipients suitable for suppositories are natural or hardened oils, waxes, fats, semiliquid or liquid polyols and the like.

The pharmaceutical preparations may moreover contain preservatives, solubilizers, stabilizers, wetting agents, emulsifiers, sweeteners, colors, aromatizing agents, salts to alter the osmotic pressure, buffers, coating agents and/or antioxidants.

The following examples illustrate the invention.

EXAMPLE 1

Lacquered tablets of the following composition were produced:

| | |
|---|---|
| Compound 23 | 300.0 mg |
| Anhydrous lactose | 30.0 mg |
| Microcrystalline cellulose | 30.0 mg |
| Polyvinylpyrrolidone | 20.0 mg |
| Magnesium stearate | 5.0 mg |
| Polyethylene glycol 6000 | 0.8 mg |
| Yellow iron oxide | 1.2 mg |
| Titanium dioxide | 0.3 mg |
| Talc | 0.7 mg |

Compound 23, the lactose, the cellulose and the polyvinylpyrrolidone are wet-granulated and dried. The sieved granules are mixed with the magnesium stearate, and the mixture is compressed to oval tablet cores each weighing 390.0 mg. The cores are then lacquer-coated until the lacquered tablets have reached a final weight of 400 mg.

EXAMPLE 2

Lacquered tablets were produced in analogy to Example 1 but contained 300 mg of Compound 26 in place of 300 mg of Compound 23.

EXAMPLE 3

Production of hard gelatin capsules of the following composition:

| | |
|---|---|
| Compound 23 | 250.0 mg |
| Crystalline lactose | 18.0 mg |
| Polyvinylpyrrolidone | 15.0 mg |
| Microcrystalline cellulose | 17.5 mg |
| Sodium carboxymethyl starch | 10.0 mg |
| Talc | 0.7 mg |
| Magnesium stearate | 3.0 mg |

The first five ingredients are wet-granulated and dried. The granules are mixed with the sodium carboxymethyl starch, the talc and the magnesium stearate, and the mixture is packed into size 0 hard gelatin capsules.

We claim:

1. A method of treating a patient having hyperlipidemia comprising administering a therapeutically effective amount of an endothelin antagonist to said patient.

2. The method of claim 1 wherein the endothelin antagonist is endothelin$_A$ or mixed endothelin$_{A/B}$.

3. The method of claim 1 wherein the endothelin antagonist is:

TBC-11251,

BMS-193884,

BMS-207940,

BQ-123,

SB-209670,

SB-217242,

SB-209598,

TAK-044,

Bosentan,

PD-156707,

L-749329,

L-754142,

ABT-627,

A-127772,

A-206377,

A-182086,

EMD-93246,

EMD-122801,

ZD-1611,

AC610612,

T-0201,

J-104132,

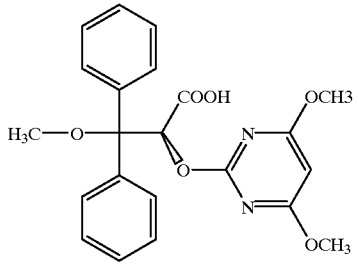

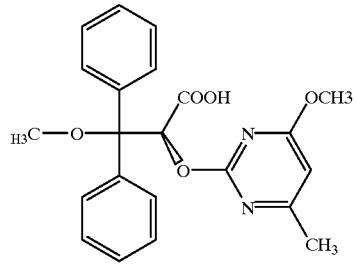

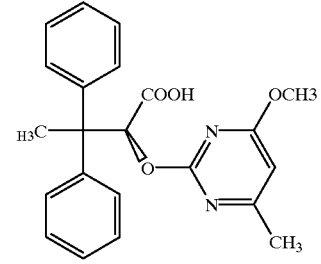

or

-continued
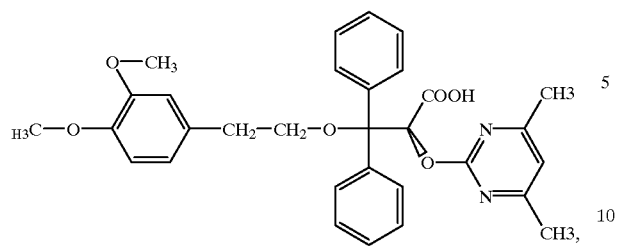
4. The method of claim 3 wherein the endothelin antagonist is
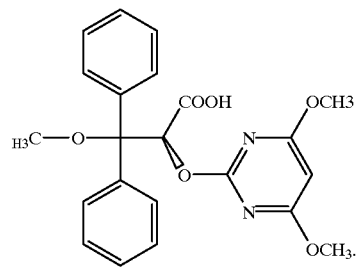
* * * * *

UNITED STATES PATENT AND TRADEMARK OFFICE
CERTIFICATE OF CORRECTION

PATENT NO.    : 6,197,780 B1
DATED         : March 6, 2001
INVENTOR(S)   : Muenter et al.

It is certified that error appears in the above-identified patent and that said Letters Patent is hereby corrected as shown below:

Column 4, claim 3,
Line 31, "AC610612," should be -- AC-610612, --.
Lines 46-65, the two formulas should read:

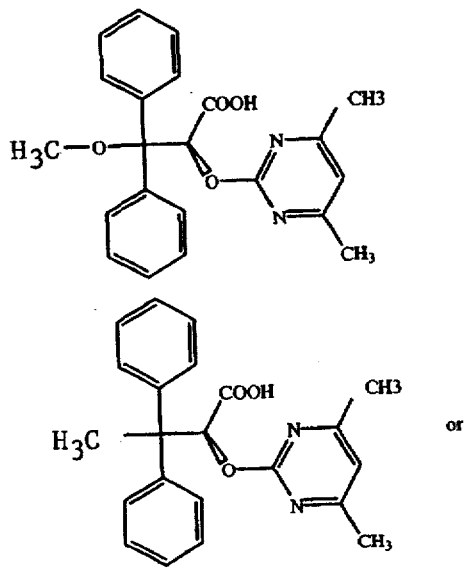

Column 5, claim 3,
Lines 1-10, the formula should read:

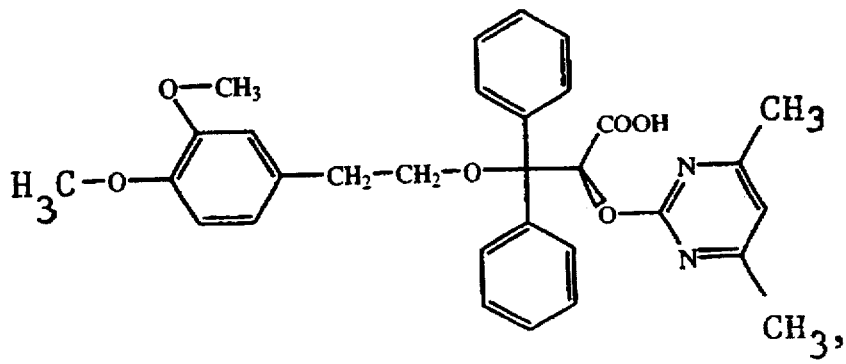

UNITED STATES PATENT AND TRADEMARK OFFICE
CERTIFICATE OF CORRECTION

PATENT NO.   : 6,197,780 B1
DATED        : March 6, 2001
INVENTOR(S)  : Muenter et al.

It is certified that error appears in the above-identified patent and that said Letters Patent is hereby corrected as shown below:

Column 6, claim 4,
Lines 1-10, the formula should read:

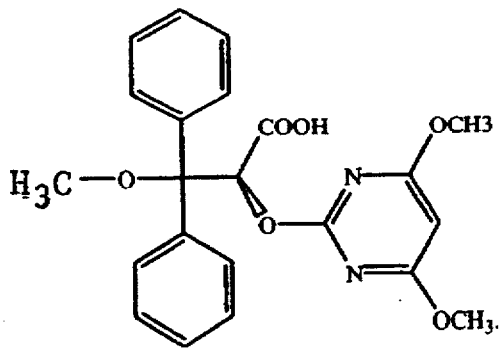

Signed and Sealed this

Fifth Day of February, 2002

Attest:

JAMES E. ROGAN
*Attesting Officer*    *Director of the United States Patent and Trademark Office*